United States Patent [19]

Fischer

[11] 4,003,371

[45] Jan. 18, 1977

[54] LOW PRESSURE HYPERBARIC CHAMBER

[76] Inventor: Boguslav H. Fischer, 251 E. 32nd St., New York, N.Y. 10016

[22] Filed: Jan. 28, 1976

[21] Appl. No.: 653,199

Related U.S. Application Data

[63] Continuation-in-part of Ser. No. 549,608, Feb. 13, 1975, abandoned.

[52] U.S. Cl. ................................ 128/184; 128/186; 128/299; 128/30.2; 128/204

[51] Int. Cl.[2] ........................................ A61M 13/00

[58] Field of Search .......... 128/204, 299, 298, 297, 128/191 A, 30, 30.2, 38, 39, 40, 1 B, 184, 172, DIG. 20, DIG. 15

[56] References Cited

UNITED STATES PATENTS

| | | | |
|---|---|---|---|
| 2,134,646 | 10/1938 | Sauzedde | 128/38 |
| 2,822,803 | 2/1958 | Huxley et al. | 128/30 |
| 3,217,707 | 11/1965 | Werding | 128/38 |
| 3,345,985 | 10/1967 | Fisher | 128/204 |
| 3,744,491 | 7/1973 | Fischer | 128/184 |
| 3,786,809 | 1/1974 | Kitrilakis | 128/191 A |

*Primary Examiner*—Robert W. Michell
*Assistant Examiner*—Henry J. Recla
*Attorney, Agent, or Firm*—DeLio and Montgomery

[57] ABSTRACT

A portable chamber for enclosing a portion of the body, such as the lower leg, for treatment with oxygen or other gas at pressures above atmospheric, the chamber having a closed end and a limb-receiving sleeve in its entrance end, the sleeve being inflatable to ensure effective closing off of the chamber from ambient air, for maintaining desired pressure in the chamber and preventing uncontrolled escape of the gas while eliminating the danger of too tight binding of the limb. Simple means for controlling pressure and humidity may be provided.

8 Claims, 14 Drawing Figures

LOW PRESSURE HYPERBARIC CHAMBER

This application is a continuation-in-part of application Ser. No. 549,608, filed Feb. 13, 1975, now abandoned.

This invention relates to a portable hyperbaric chamber for enclosing a portion of the body such as the lower leg, for treatment with oxygen or other gas at somewhat elevated pressures, the chamber having a closed end and an open, limb-receiving end, the latter being provided with an entrance sleeve and means, preferably inflatable, to hold the sleeve sealingly but resiliently against the limb. The treatment gas may conveniently be used also for inflation and humidification. This chamber is an improvement over the chamber disclosed in applicant's U.S. Pat. No. 3,744,491, July 10, 1973, which patent sets forth the background of the invention.

It is an object of the invention to provide a chamber with simple and effective means for sealing the entrance sleeve against the skin surface of the limb during treatment.

It is another object of the invention to provide a sectional chamber having adequate sealing means at all points to prevent the leakage of gas from the chamber, thus ensuring maintenance of the described pressure.

It is a further object of the invention to provide entrance sealing means which is self-adjusting to have a close fit against the skin surface without being tight enough to cut off or significantly impair the circulation of blood.

It is yet another object of the invention to provide a chamber and sealing means therefor which are simple in construction and operation, for handling by relatively untrained personnel with complete safety of the patient.

It is a further object of the invention to provide simple and efficient humidifying means, in series with the gas supply.

It is a still further object to provide certain improvements in the form, construction and arrangement of the several parts whereby the above named and other objects may effectively be obtained.

The invention accordingly comprises the features of construction, combination of elements, and arrangement of parts which will be exemplified in the construction hereinafter set forth, and the scope of the invention will be indicated in the claims.

A practical embodiment of the invention is shown in the accompanying drawings, wherein.

Figure 1:
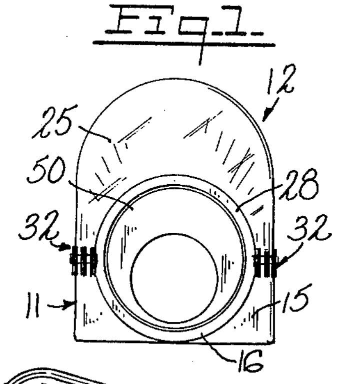
FIG. 1 represents an entrance end elevation of the chamber.

Referring to the drawings, and particularly FIGS. 1 to 5, the chamber comprises two main parts, a lower flat bottomed tray portion 11 and an upper hood portion 12. The tray portion has vertical side walls 13 which diverge somewhat from the entrance end to the closed end, a vertical closed end wall 14, and a vertical entrance end wall 15 in which is installed the lower semicircular half 16 of the entrance assembly mounting socket. The upper edges of the walls 13 and 14, and of the socket half are provided with an upwardly facing groove 17 in which is fitted a resilient sealing strip or gasket 18. The socket half includes radially inwardly projecting semi-annular ridges 19, 20 which define a generally V-shaped groove 21 having a flat bottom 22.

The hood portion 12 is preferably of transparent rigid plastic material, having a semi-cylindrical body portion 25 and an integral closed end wall 26, the body portion flaring upward and laterally so that its sides 27 conform to the side walls 13 of the lower portion. At its entrance end the body portion 25 merges with the upper semicircular half 28 of the entrance assembly mounting socket, which socket half is complementary to the lower socket half 16 and is provided with matching ridges 29, 30 defining a matching groove 31.

Figure 2:
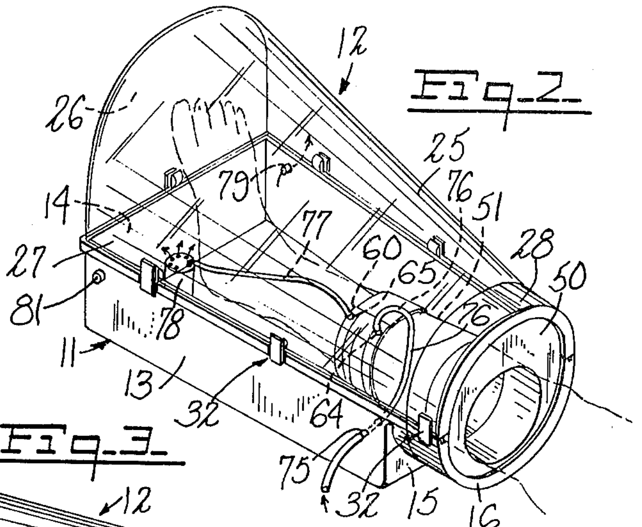
FIG. 2 represents a perspective view of the chamber, in use.
Figure 4:
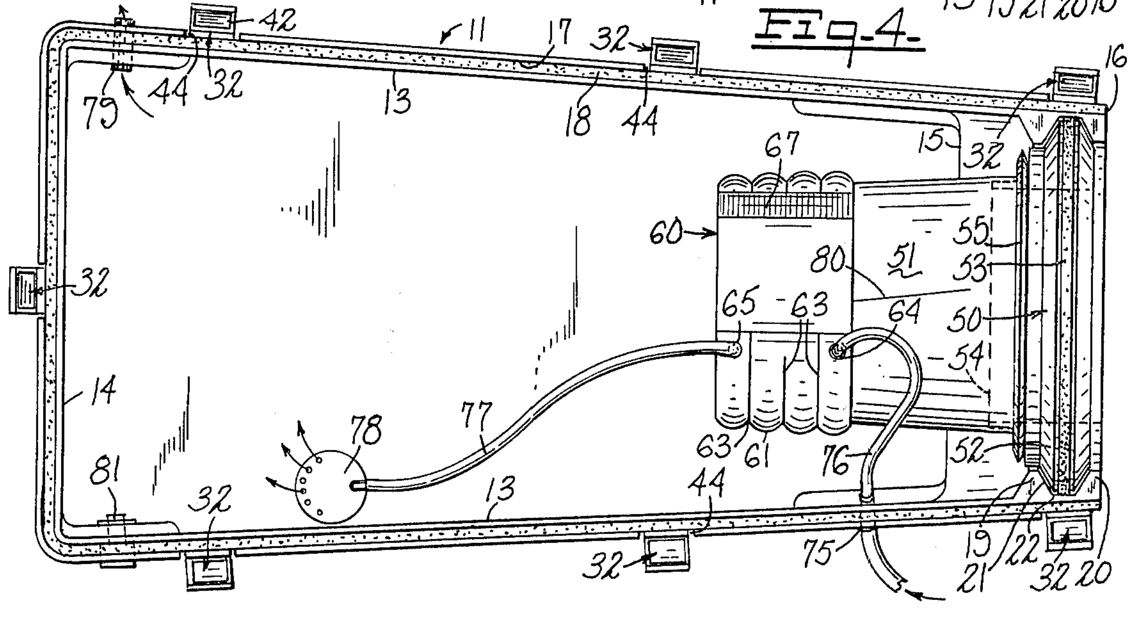
FIG. 4 represents a top plan view of the lower chamber portion, the upper portion being removed and the entrance sealing assembly being in place.
Figure 5:
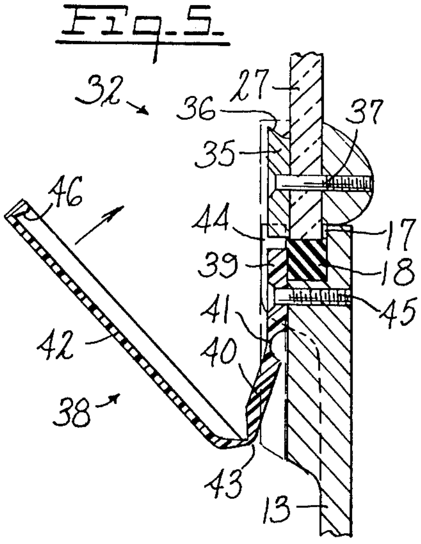
FIG. 5 represents a detail vertical section on the line V—V of FIG. 3.

The lower edges of the wall 26, sides 27 and socket half 28 are so disposed that they can rest evenly on the gasket 18, and they are held in sealing engagement therewith by clips 32. Such clips may be of metal or plastic, of various types, but a suitable all-plastic toggle clip is shown in detail in FIG. 5, the clips being disposed three on each side and one on the closed end (FIGS. 2 and 4). Each clip comprises a fixed part in the form of a square block 35 having its upper edge beveled to form a lip 36 and being fixed at selected points to the outer surfaces of the sides 27 and end wall 26, adjacent the lower edges thereof. The blocks 35 may be secured by cementing and/or by means of screws 37. The movable part 38 of the clip is of a flexible but relatively inextensible plastic material having a mounting tab 39 at one end, a toggle link 40 connected to the tab 39 by a hinge 41 and a latch bar 42, connected to link 40 by the hinge 43. The outer wall of the groove 17 is cut away at each clip position and the mounting tabs 39 are secured in the recesses 44 thus formed by cementing and/or by means of screws 45. Each latch bar 42 is provided with a hook 46 at its free end, adapted to engage securely over the lip 36, and at its hinge end the latch bar is bent at an angle sufficient to place the hinge 43 inwardly (toward the link 40) from the plane of the latch bar. From observation of FIG. 5 it will be understood that the tight latching can be effected by engaging the hook 46 over the lip 36 (as indicated in broken lines) and pressing inward the hinge end of the latch bar so that the hinge 43 snaps past the center line defined by the point of hook-lip engagement (46–36) and the first hinge 41.

Figure 3:
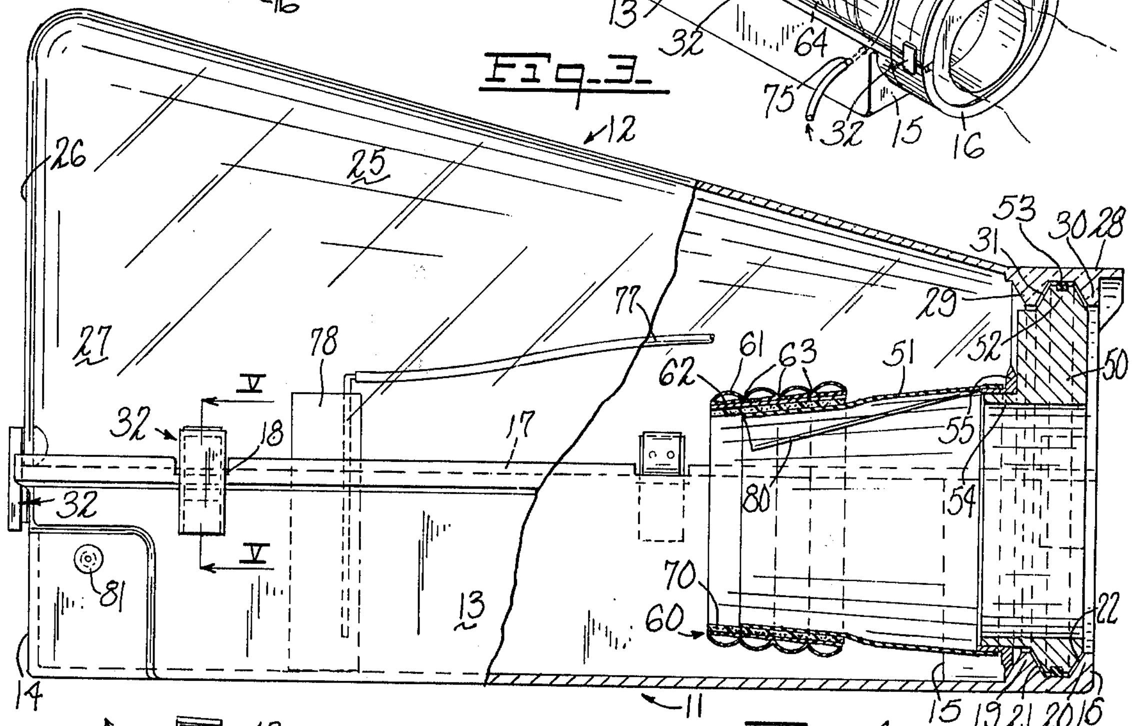
FIG. 3 represents a side elevation, partly in vertical section, of the chamber.
Figure 6:
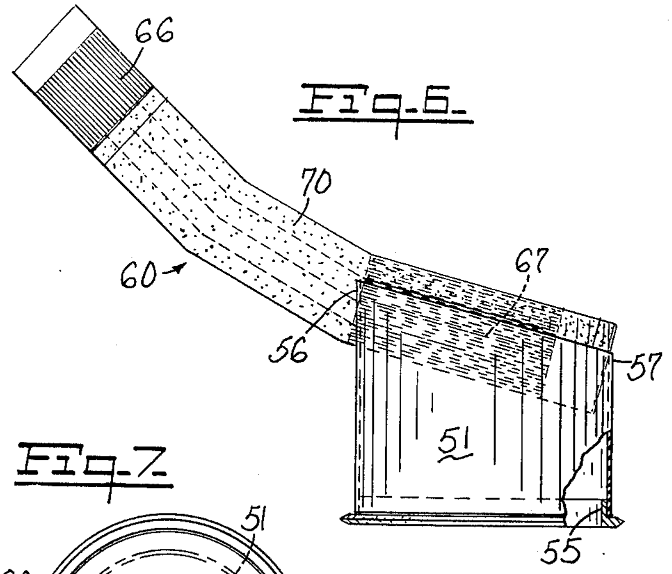
FIG. 6 represents a detail elevation of the sealing sleeve with the inflatable band attached and extended.
Figure 7:
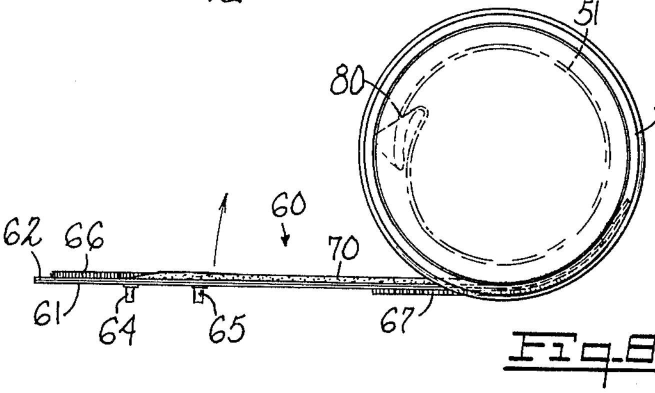
FIG. 7 represents a plan view of the parts shown in FIG. 6, looking upward, with the "tucked" position of the sleeve indicated in broken lines.
Figure 8:
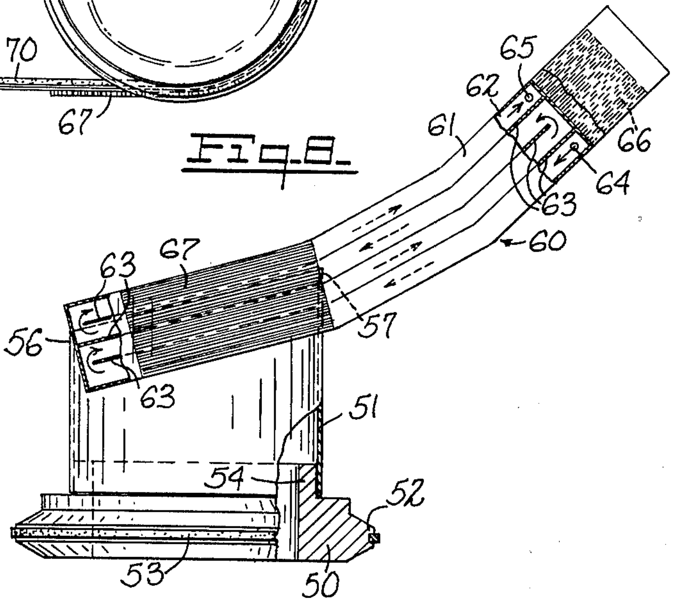
FIG. 8 represents a detail side elevation of the entrance sealing assembly, parts being broken away and parts being shown in section.
Figure 9:
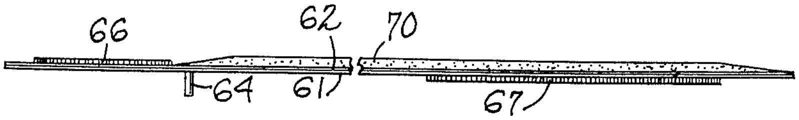
FIG. 9 represents a side elevation of the inflatable band alone, parts being broken away.

The parts referred to as the entrance assembly comprise the circular hub 50 and the cylindrical sleeve 51 of foldable plastic material. The hub 50 is formed with an annular grooved ridge 52 having a compressible gasket 53 fitted in its groove, and with an annular axially projecting collar 54. The sleeve 51 is or may be mounted on a ferrule 55 (FIGS. 6 and 7) adapted to have a tight friction fit on the collar 54 (FIG. 3). If the ferrule is omitted, the sleeve may be fixed directly on the collar 54, as in FIGS. 8 and 10. The free end of the sleeve is preferably cut on a slant, having a high side 56 and a low side 57, as shown in FIG. 6. A special means for constraining the sleeve is shown in FIGS. 6, 7 and 8 as comprising a strap 60 having double walls 61, 62 of gas-impermeable flexible material throughout most of its length, with internal dividers 63 (three being shown) arranged to provide a continuous tortuous channel from a gas inlet 64 to a gas outlet 65. The strap 60 is somewhat arcuate in plan and is secured, adjacent one end, to the outer surface of the sleeve in a position aligned with the slanting edge of the sleeve (FIGS. 6 and 8). Closure of the strap 60, in any adjusted position, is effected by means of a "Velcro" fabric area 66 on the inner surface of the strap near its free end and another Velcro fabric area 67 on the outer surface of the strap adjacent its point of attachment to the sleeve. A substantially gas-tight sealing engagement with the skin of the patient may be assured by the provision of a layer of latex 70, preferably expanded, on the inner face of the strap throughout the area not occupied by the Velcro fabric 66, as shown in FIGS. 6, 7 and 9. This achieves complete adhesion of the sleeve along the irregular curve of the limb surface.

Figure 10:
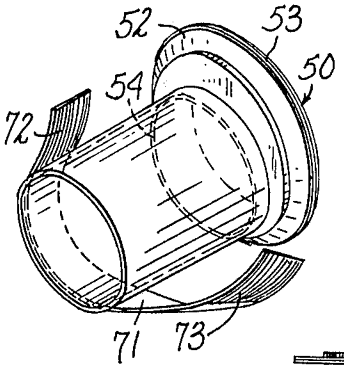
FIG. 10 represents a detal perspective view of a sealing sleeve in combination with a modified (non-inflatable) form of band.

While an inflatable strap with latex facing is preferred a plain strap 71, with Velcro fabric attaching panels 72, 73 may be substituted, as shown in FIG. 10, particularly where the required gas pressure is low. The strap 71 may be an elastic fabric, plastic web or other suitable material.

Oxygen (or other gas) is supplied to the system from a source (not shown) through an inlet fitting 75 in the wall 13 of the lower portion 11 of the chamber. The fitting 75 is connected by a short flexible tube 76 to the gas inlet 64 in the strap 60. The gas outlet 65 may open freely to the interior of the chamber but is preferably connected by a tube 77 to a humidifier or nebulizer 78, which may be of any suitable and convenient type. From the humidifier 78 the gas diffuses into the interior of the chamber, from which it is vented through the exit fitting 79 in the wall 13 diagonally opposite the inlet fitting. As a safety precaution, a blow-out plug 81 may be provided in a wall 13 of the lower tray. The pressure of gas in the chamber is controlled by a pressure-responsive valve of any suitable type, not shown, connected to the fitting 79, the range of pressures contemplated, for oxygen, being from 5 to 30 mm. Hg at a flow rate of 2 to 4 liters/min.

The operation and manner of use of the chamber are clear from the foregoing but may be summarized as including the steps of: fitting the hub 50 and sleeve 51 (the unit of FIG. 8) over the patient's limb to a point which may be, for instance, just below the knee, as shown in FIG. 2; taking a tuck 80 in the longer side 56 of the sleeve and closing the strap 60 around the sleeve in sealing engagement with the limb; placing the lower portion 11 of the chamber under the limb and fitting the hub 50 into the groove 21; connecting the hoses 76 and 77; placing the upper portion 12 of the chamber on the lower portion with its edge on the gasket 18; closing the clips 32 to hold the upper and lower portions in closed, sealed, position; starting the flow of oxygen or other gas.

The flow resistance in tube 77 and humidifier 78, though small, is sufficient to cause inflation of the strap 60 so that the sleeve 51 is held gently but firmly against the skin of the patient's limb and the exposed areas within the chamber are subjected to a gas treatment at the desired pressure for any needed period of time.

In the system described above there is the possibility that the patient's calf, if not otherwise supported, may compress the bottom portion of the strap against the floor of the chamber, thus restricting the passage of gas through the tortuous channel from inlet 64 to outlet 65. If gas supply pressure is increased to maintain the required flow to the interior of the chamber, undersirable tightening of the strap against the patient's limb may result, with possibly serious adverse effects. The alternative arrangement shown in FIGS. 11 to 14 is designed to obviate the difficulty just mentioned.

Figure 11:
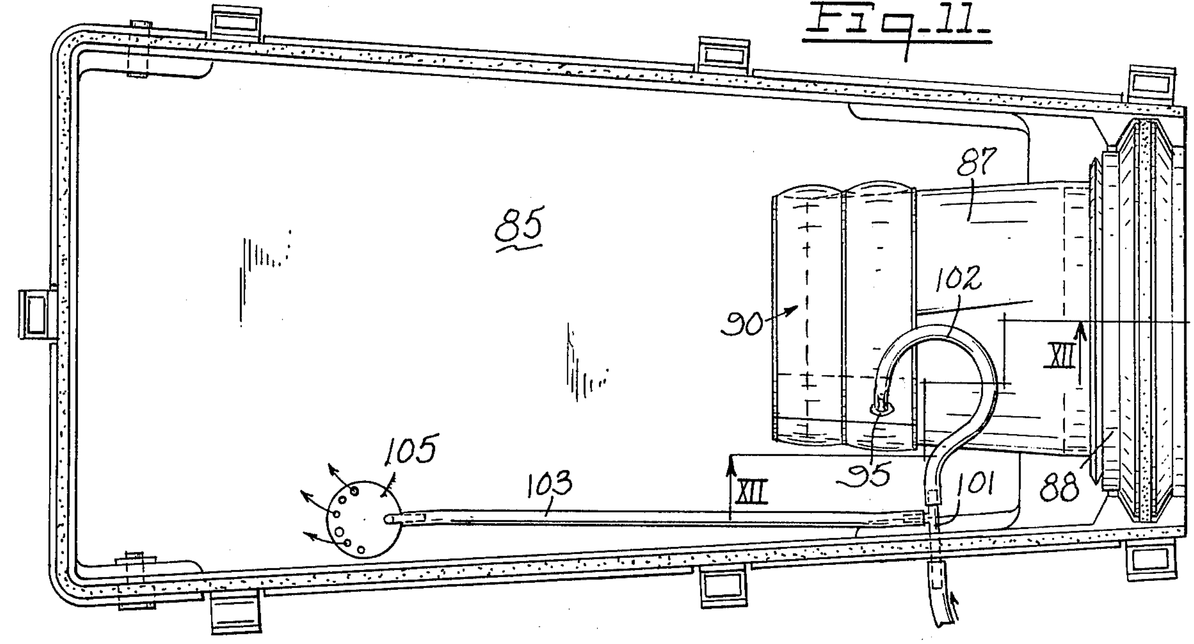
FIG. 11 represents a top plan view of the lower chamber portion, similar to FIG. 4, showing an alternative form of inflatable band and gas supply connections.
Figure 12:
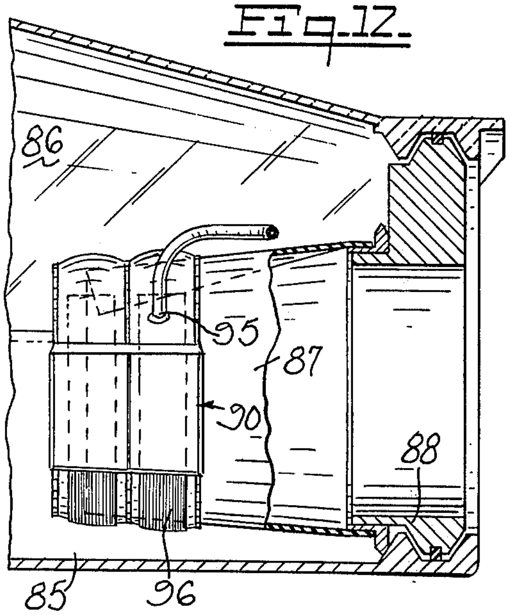
FIG. 12 represents a detail vertical section on the line XII—XII of FIG. 11 showing the inlet end of the chamber, as in FIG. 3.
Figure 13:
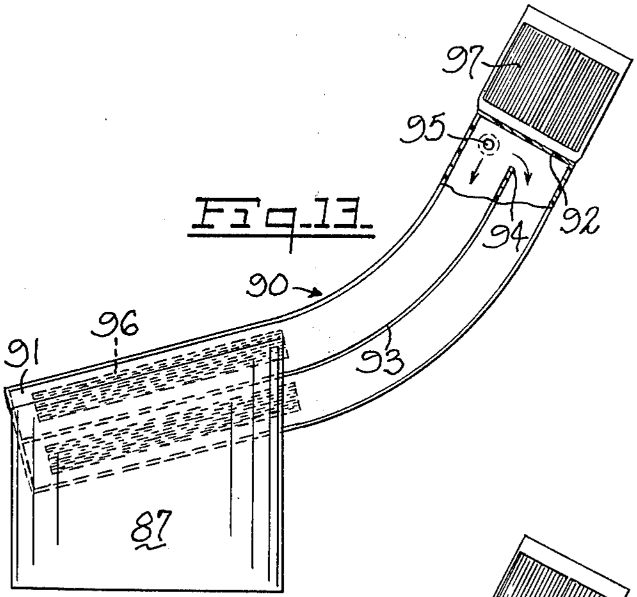
FIG. 13 represents a detail elevation of the sealing sleeve with one alternative form of inflatable band attached.

In FIGS. 11 and 12 the lower and upper chamber portions 85, 86 correspond to the portions 11 and 12 in FIGS. 1 to 4, and the sleeve 87 is mounted in a hub assembly 88 which also correspond to the sleeve 51 and hub 50.

The inflatable strap 90 is formed of two strips of gas-impervious plastic, somewhat arcuate in shape, sealed along their edges, across one end 91 and transversely also at 92 near the other end to form a closed compartment, which may be longitudinally sub-devided by the seal line 93 from the end 91 to a point 94 near the seal 92. A gas inlet 95 is provided also near the seal 92, but there is no outlet, the compartments separated by the seal line 93 constituting dead end inflatable pockets. The strap 90 may conveniently be attached to the beveled end of the sleeve 87, corresponding to the strap attachments shown in FIGS. 6 and 8, and the strap is equipped with Velcro fastening areas 96, on the outside adjacent the sleeve, and 97 on the inside at the free end.

Figure 14:
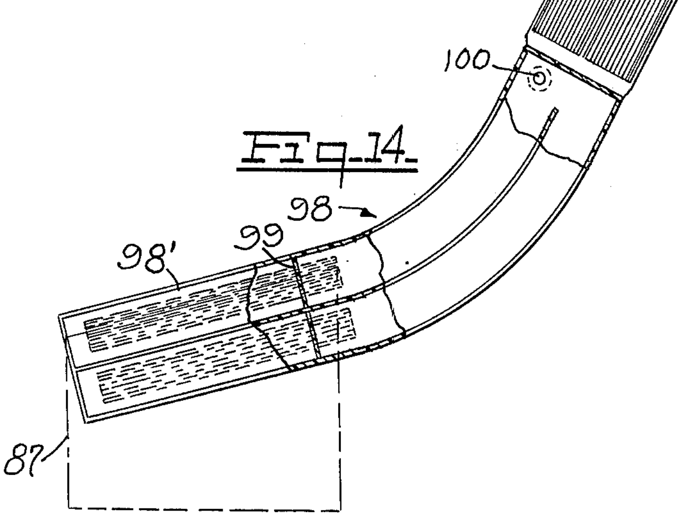
FIG. 14 represents a detail elevation, as in FIG. 13, showing another alternative form of inflatable band.

The strap 98 shown in FIG. 14 is the same as strap 90 except that the inflatable pockets are closed by a seal line 99 to leave a flat non-inflatable area 98' opposite the longer Velcro fastener at the attached end. The gas inlet is shown at 100.

The gas supply enters the lower chamber portion 85 through a T fitting 101, having a tube 102 leading to the gas inlet 95 (or 100) and a tube 103 leading to the humidifier 105, corresponding to humidifier 78 in FIGS. 3 and 4. The humidifier is of the bubbler type, or its equivalent, and is designed to maintain the humidity in the chamber, when in operation, at a level of 60 to 90%. This feature is of substantial importance since the oxygen atmosphere in the chamber tends to have a drying effect on the exposed skin of the patient's limb, with harmful results if not counteracted. Additionally, adequate humidity is needed to prevent the build-up of static electric charges which could cause explosions and fires. The humidifier could, if desired, be provided with a separate gas supply line.

The straps 90 or 98 are applied to the patient's limb in such a position that little, if any, of the inflated area is beneath the limb, the inflation of the strap taking place for the most part in an arc of 180°, more or less, extending across the top of the limb and down one or both sides. A low but adequate sealing pressure can thus be maintained without danger of undue tightening.

The chamber, as shown, is designed to accommodate most conveniently a patient's foot and lower leg, but the same chamber could receive as well (with or without installing a smaller sleeve) the hand and lower arm. Similar parts could, however, be designed on a larger scale to receive the lower half of the body, with a sleeve sealing around the patient's waist. Even on such an enlarged scale, a chamber constructed as disclosed herein would be substantially less expensive than the "total containment" chambers discussed in applicant's prior U.S. Pat. No. 3,744,491, but the greatest utility of the present chamber probably lies in the limb treatment field.

It may thus be seen that the objects of the invention set forth, as well as those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

What I claim is:

1. A low pressure hyperbaric chamber for treatment of a part of a patient's body comprising, an elongated enclosure having a closed end and an entrance end, said enclosure including separable lower and upper portions, means for releasably holding said portions in sealing engagement, the enclosure being provided with a gas supply passage and a gas exit passage, the entrance and being adapted to permit introduction of said body part into the enclosure and being provided with a tubular sleeve of foldable material mounted in said entrance end, an annular hub adapted to be fitted in the entrance end of the enclosure, the sleeve being mounted at one end on the hub and the other end of the sleeve projecting freely into the chamber, the freely projecting end being cut on a slant, and inflatable securing means for closing said end sealingly and resiliently around said body part.

2. A hyperbaric chamber according to claim 1 wherein the securing means is an inflatable strap containing at least one gas passageway provided with a gas inlet.

3. A hyperbaric chamber according to claim 2 wherein the strap is attached to the sleeve, the attached portion of the strap lying parallel to the slant cut end of the sleeve.

4. A hyperbaric chamber according to claim 2 wherein the gas supply passage is connected to the gas inlet on the inflatable strap.

5. A low pressure hyperbaric chamber for treatment of a part of a patient's body comprising, an elongated enclosure having a closed end and an entrance end, said enclosure including separable lower and upper portions, means for releasably holding said portions in sealing engagement, a gas supply passage and a gas exit passage, the entrance end being adapted to permit introduction of said body part into the enclosure and being provided with a tubular sleeve of foldable material mounted at one end in said entrance end, the other end of the sleeve projecting freely into the chamber, an inflatable strap containing at least one gas passageway provided with a gas inlet, said strap being attached adjacent one of its ends to the sleeve adjacent said other end of the sleeve, the gas supply passage being connected to said gas inlet, a humidifier, and means connecting the gas supply passage to said humidifier.

6. A low pressure hyperbaric chamber according to claim 5 wherein the strap is provided with at least one gas passageway disposed longitudinally thereof.

7. A low pressure hyperbaric chamber according to claim 6 wherein the gas passageway extends along only a portion of the effective length of the strap.

8. A low pressure hyperbaric chamber according to claim 6 wherein the gas supply passage is connected to one conduit communicating with the gas inlet on the strap and to a second conduit communicating with the interior of the enclosure.

* * * * *

UNITED STATES PATENT AND TRADEMARK OFFICE
CERTIFICATE OF CORRECTION

PATENT NO. : 4,003,371

DATED : January 18, 1977

INVENTOR(S) : Boguslav H. Fischer

It is certified that error appears in the above-identified patent and that said Letters Patent are hereby corrected as shown below:

Column 2, line 6, "detal" should read --detail--.

Column 4, line 38, "sub-dev-" should read "sub-div-".

Column 5, line 8 of claim 1, "and" should read --end--.

Column 6, line 6 of claim 5, after "engagement," insert --the enclosure being provided with--.

Signed and Sealed this

Fifth Day of April 1977

[SEAL]

*Attest:*

RUTH C. MASON
*Attesting Officer*

C. MARSHALL DANN
*Commissioner of Patents and Trademarks*